United States Patent [19]
Baumgartner et al.

[11] Patent Number: 6,076,659
[45] Date of Patent: Jun. 20, 2000

[54] PACKAGING FOR SURGICAL SUTURE MATERIAL

[75] Inventors: Karl-Heinz Baumgartner, Wedel; Kay van der Wolk, Lubeck; Jorg Lienhoft, Labatz, all of Germany

[73] Assignee: Ethicon, Inc., Somerville, N.J.

[21] Appl. No.: 09/217,317

[22] Filed: Dec. 21, 1998

[51] Int. Cl.[7] .................................................. A61B 17/06
[52] U.S. Cl. .......................................... 206/63.3; 206/339
[58] Field of Search .................................... 206/63.3, 227, 206/339, 380, 382

[56] References Cited

U.S. PATENT DOCUMENTS

| | | | |
|---|---|---|---|
| 3,972,418 | 8/1976 | Schules et al. | 206/63.3 |
| 5,129,511 | 7/1992 | Brown et al. | 206/63.3 |
| 5,222,978 | 6/1993 | Kaplan et al. | 206/63.3 X |
| 5,246,104 | 9/1993 | Brown et al. | 206/63.3 |
| 5,350,060 | 9/1994 | Alpen et al. | 206/63.3 |
| 5,366,081 | 11/1994 | Kaplan et al. | 206/339 |
| 5,462,162 | 10/1995 | Kaplan et al. | 206/339 |
| 5,468,252 | 11/1995 | Kaplan et al. | 206/63.3 X |
| 5,628,395 | 5/1997 | Daniele et al. | 206/63.3 |
| 5,704,469 | 1/1998 | Daniele et al. | 206/63.3 |

*Primary Examiner*—Bryon P. Gehman
*Attorney, Agent, or Firm*—Emil Richard Skula

[57] ABSTRACT

A packaging for surgical suture material has a base sheet from which a wall extends in a spiral manner, the wall defining a thread duct. The thread duct opens at its first end into a thread-removal area. A cover is located above the thread duct. The spiral wall is provided on its outward-facing side with thread-deflector protrusions spaced apart from one another in the course of the thread duct.

18 Claims, 5 Drawing Sheets

PACKAGING FOR SURGICAL SUTURE MATERIAL

TECHNICAL FIELD

The invention relates to a packaging (package container) for surgical suture material.

BACKGROUND OF THE INVENTION

A packaging for surgical suture material is known from DE-AS 1 466 808 and from U.S. Pat. No. 3,338,401 which is parallel to it, in which a wall extending like a spiral rises from a base sheet. This wall defines a spiral-like thread duct which opens at its first end into a thread-removal area. A cover is provided for the thread duct. In order to remove surgical suture material, e.g. a surgical thread or a surgical thread to one end of which a surgical needle is secured, from the packaging, the end of the thread projecting into the thread-removal area or the surgical needle is grasped and the thread is then drawn out of the thread duct through the first end of the thread duct.

A drawback in the case of the previously known packaging for surgical suture material is that, when the surgical suture material is being removed, the thread can pull tight in the thread duct, in which it is guided over several spiral turns. Furthermore, in the attempt to remove it from the packaging, the thread can move inside the thread duct into the border area between the wall extending like a spiral and the cover, where a gap is frequently formed because of the production process. The thread can jam there, which makes the further removal of the surgical suture material much more difficult.

DISCLOSURE OF THE INVENTION

The object of the invention is to further develop a packaging for surgical suture material of the type described above in such a way that surgical suture material situated in the packaging can be removed without problems.

This object is achieved by a packaging for surgical suture material having the features of claim 1. Advantageous designs are given in the dependent claims.

The packaging according to the invention for surgical suture material has a base sheet from which a wall extending like a spiral rises. The wall extending like a spiral defines a spiral-like thread duct which opens at its first end into a thread-removal area. A cover is provided for the thread duct. The wall is provided on its outward-facing side with thread-deflector protrusions which are spaced apart from one another along the course of the thread duct.

The effect of the thread-deflector protrusions is that a surgical thread, when it is to be drawn from the thread duct upon the removal of the surgical suture material, is not pressed over the whole length of its section situated in the thread duct against the outward-facing side of the wall, as would otherwise be the case per se as a result of the forces occurring when the thread is pulled through a spiral-like thread duct ("capstan effect"), but is repeatedly guided away from the outward-facing side of the wall by the thread-deflector protrusions. The frictional forces occurring when the thread is being removed are thereby greatly reduced, the thread has less of a tendency to wander into the border area between the wall and the cover, and the surgical suture material can be removed from the packaging without problems.

In a preferred version, the cover has a lip which is matched to the course of the wall and which rests against the outward-facing side of the wall in the thread duct and is provided in the region of the thread-deflector protrusions with recesses into which the thread-deflector protrusions project. With such a design, the thread-deflector protrusions completely prevent a thread from becoming caught between the lip and the wall when surgical suture material is removed. The transition zone between the wall and the cover can therefore cause no problems whatsoever when surgical threads are drawn out of the thread duct. Parallel to the lip, the cover preferably has a second lip which rests against the inward-facing side of the wall in the thread duct. In this case, both lips fix the wall against the cover, as a result of which the stability of the packaging is increased and a seal is effected between the wall and the cover.

The thread-deflector protrusions can have a wedge-like design, in which case the apex of the wedge angle in question points towards the first end of the thread duct. This design makes it easy to fill the packaging with surgical suture material if surgical threads are introduced into the thread duct via the first end of the thread duct, as the ends of the surgical threads can slide problem-free along thread-deflector protrusions which are shaped in this way.

In a preferred version, frictional forces are also reduced when the surgical suture material is removed if, along the course of the thread duct, the transitions between the base sheet and the wall and/or the transitions between the wall and the cover are of rounded design.

The base sheet and/or the cover preferably have an opening in the region of the second end of the thread duct. When the surgical suture material is packed into the packaging, the base sheet with the wall extending like a spiral and the cover already being firmly connected to each other, a negative pressure is applied to this opening. The thread ends which are not to come to rest in the thread-removal area are introduced into the thread duct via the first end of the thread duct, and sucked into the thread duct by the negative pressure. In this way, the surgical threads can be introduced into the thread duct quickly, reliably and without becoming tangled in the process.

In a preferred version, the thread-removal area is arranged in the zone surrounded by the thread duct, the cover preferably leaving the thread-removal area at least partly exposed. In other words, the thread-removal area is situated in the central section of the packaging, and the thread-removal area is preferably freely accessible without hindrance through the cover. With this geometry, the spiral-like thread duct has smaller radii in the vicinity of its first end, that is in the vicinity of the thread-removal area, than in the vicinity of its second end. This brings about a better thread run when the threads are being drawn out, but also when the packaging is being packed with surgical suture material. The greater the radii of the thread duct, the smaller the so-called thread memory effect, i.e. the tendency of a surgical thread, after it has been removed from the packaging, to reassume the position which it had inside the packaging.

A wedge-shaped ramp, which is preferably designed in one piece with the base sheet, can be arranged at the base sheet in the thread-removal area. If there are several surgical threads in the thread duct which are not fitted with surgical needles, the ramp makes it easier to remove individual threads. To this end, the bundle of threads projecting from the first end of the thread duct is rotated onto the ramp with the thumb and moved over it. In the process, the thread bundle is fanned out, with the result that the ends of individual threads can be grasped without problems in order to draw the thread concerned out of the thread duct. It is advantageous if a tongue starting from the cover projects into a recess provided at the ramp. The tongue prevents a surgical thread from becoming caught between the ramp and the cover when the thread bundle fans out. A thread-holder is preferably assigned to the ramp.

If surgical suture material which has threads fitted with surgical needles is to be housed in the packaging, in a preferred version a mounting for holding one or more surgical needles is arranged in the thread-removal area at the base sheet, which mounting is preferably designed in one piece with the base sheet. A supporting strip for one or more surgical needles can be arranged at the base sheet, which strip is preferably designed in one piece with the base sheet. One or more surgical needles can be positioned ready for use in the packaging with the help of the mounting. This makes possible a simple and precise removal of individual needles with threads. If the mounting is designed in one piece with the base sheet, no additional materials need be used for the mounting, which reduces production costs and makes for environmentally friendly disposal. The supporting strip is preferably so arranged that it extends essentially perpendicular to the surgical needles. A gap relative to the top face of the base sheet is thereby maintained, with the result that a surgical needle can be grasped without problems in the area between the supporting strip and the mounting and removed without slipping or tilting in the process.

As already indicated, the thread duct can be adapted to house several surgical threads. For this purpose it should have a width and a height which are a multiple of the thread thickness. Tests have shown that twelve or even more threads can be contained in the thread duct without the removal of individual threads being hampered to any noteworthy extent by the proximity of the other threads. The threads remaining in the thread duct essentially maintain their original position and experience minor slippage at most. This favourable behaviour is also brought about not least by the thread-deflector protrusions. The surgical threads preferably lie not folded in the thread duct, but the thread duct has an overall length which is at least as great as the length of the housed surgical threads (e.g. 45 cm or 70 cm).

The base sheet and the wall are preferably designed integral with each other. The cover and the wall can be connected to each other by means of catches and/or protrusions, preferably shaped like rivets, which engage in recesses. In a preferred version, the base sheet with wall and the cover are each produced as an injection moulding, wherein the injection mouldings can consist of polypropylene and/or polyethylene. Injection mouldings can be produced cheaply and with high precision. The use of the fewest possible different materials likewise contributes to the reduction in production costs and also to a reduction in environmental pollution when the packaging is disposed of.

A top layer can be provided above the thread-removal area. The top layer can for example be made from cardboard and be designed to be folded back, or it can be laid on the cover and locked at the cover with noses formed from the top layer. The top layer offers a mechanical protection for the thread-removal area and the surgical threads or needles and yet, if it is designed to be folded back or removed from the thread-removal area, still permits rapid access to the thread-removal area. A product label can be located on the top layer or the cover.

An outer envelope, guaranteeing sterility, which can have e.g. an aluminium foil or an aluminized foil, is preferably provided for the packaging.

The invention is described in more detail in the following with reference to embodiments.

BEST MODE FOR CARRYING OUT THE INVENTION

Figure 1:
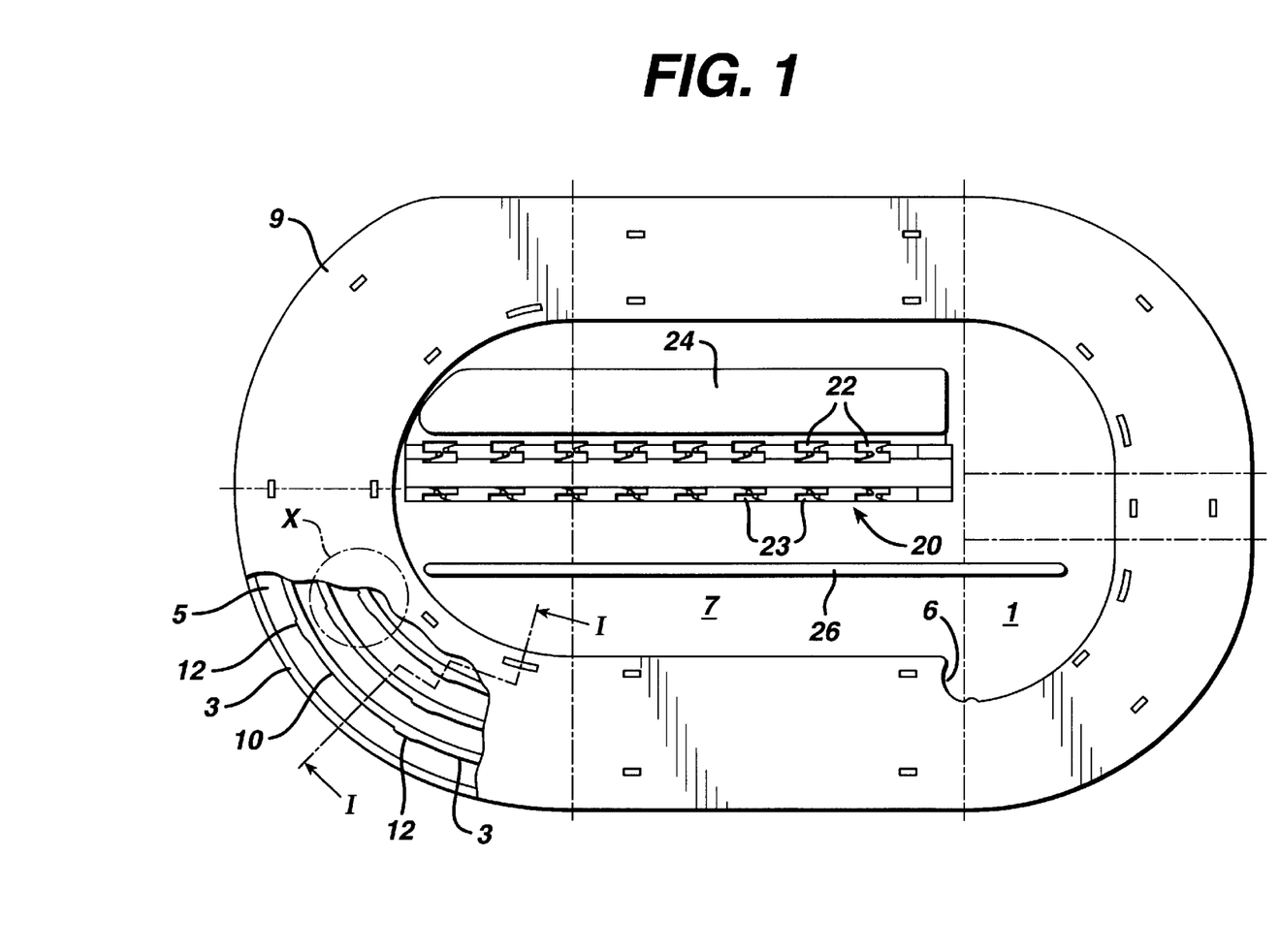
FIG. 1 a top view, partly presented as a section, of a first version of the packaging according to the invention for surgical suture material, FIG. 2 a longitudinal section through the packaging according to FIG. 1 along the section line I—I which is drawn in staggered in FIG. 1, FIG. 3 a section through the packaging according to FIG. 1 parallel to the paper plane from FIG. 1 in the area designated X in FIG. 1 at the level of the arrow A from FIG. 2, FIG. 4 a section through the packaging according to FIG. 1 parallel to the paper plane from FIG. 1 in the area designated X in FIG. 1 at the level of the arrow B from FIG. 2, FIG. 5 a top view of a second version of the packaging according to the invention for surgical suture material, which is provided with a mounting for holding several surgical needles, the cover being removed, FIG. 6 a top view of a third version of the packaging according to the invention for surgical suture material, which is designed for surgical threads not provided with surgical needles, FIG. 7 a perspective partial view of the packaging according to FIG. 6 in the region of the zone designated Z in FIG. 6, FIG. 8 a top view of the packaging according to FIG. 6, the packaging being orientated as in FIG. 6 and being provided with an envelope guaranteeing sterility, and FIG. 9 a longitudinal section through the packaging according to FIG. 6 in the envelope along the line VIII—VIII from FIG. 8.

A first version of a packaging for surgical suture material, seen from above, is represented in FIG. 1. The packaging has a base sheet 1, see also FIG. 2, from which there rises a wall 3 which extends like a spiral and is connected to the base sheet 1 in one piece in the embodiment, see FIG. 1 and FIG. 2. A spiral-like thread duct 5 is defined by the wall 3, see FIG. 1 and FIG. 2, but in particular FIG. 5, which shows a second version of the packaging for surgical suture material, viewed from above, which differs from the first version essentially only as regards the proportions. As can be seen with the help of the axes drawn in dotted lines in FIG. 1, the thread duct 5 has an asymmetrical design in the embodiment.

The first end 6 of the thread duct 5 opens into a thread-removal area 7 which in the embodiments is arranged in the zone surrounded by the thread duct 5. The second end of the thread duct 8 is closed, see FIG. 5. The thread duct 5 is closed to the top by a cover 9 which is designed as a sheet in the embodiments, see in particular FIG. 2. In its central section the cover 9 has a large opening which permits free access to the thread-removal area 7 from above.

Figures 2, 3:
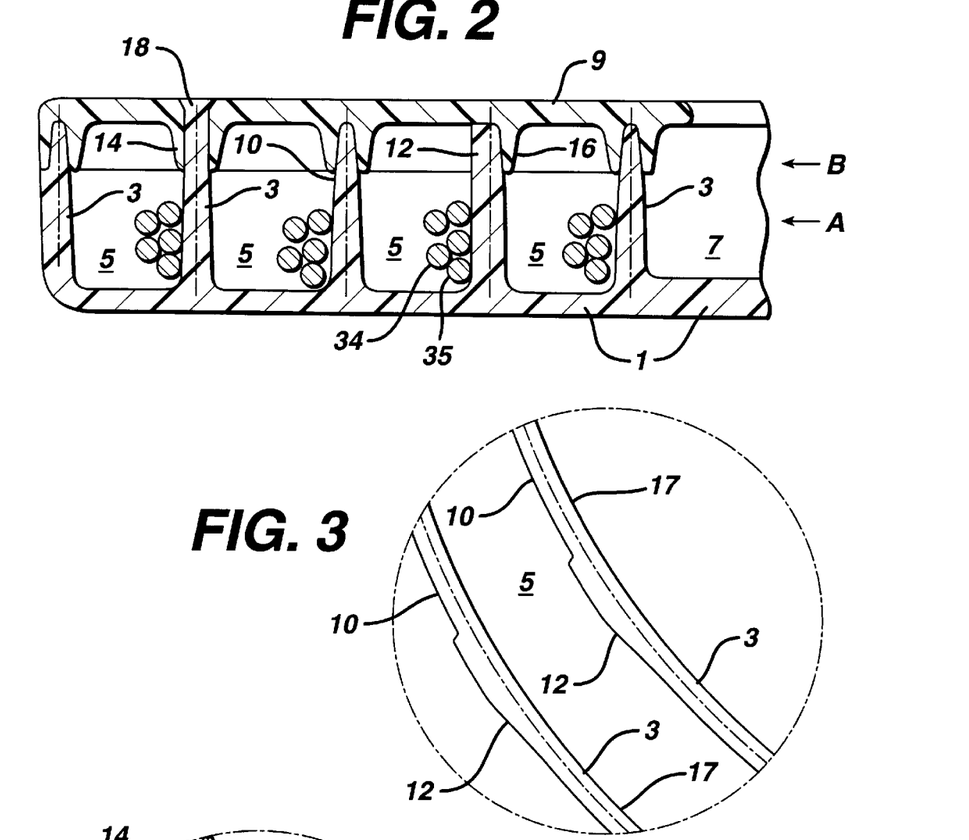
Figure 4:
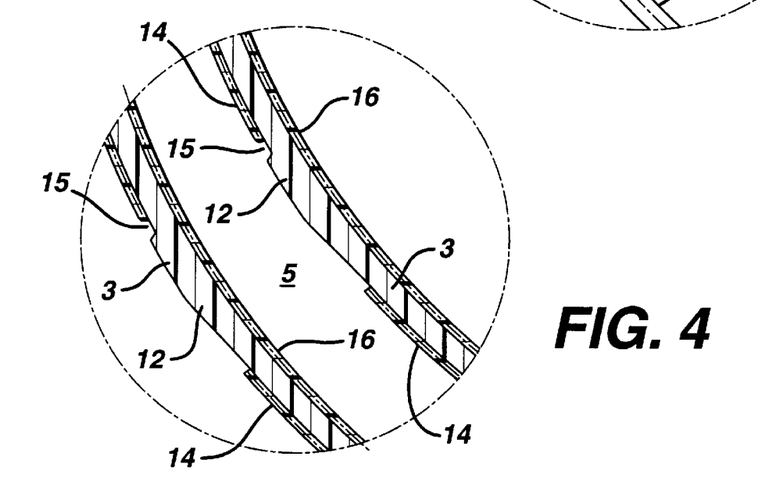

On its outward-facing side 10 the wall 3 has thread-deflector protrusions 12 which are spaced apart from one another along the course of the thread duct 5. In the first version of the packaging for surgical suture material, the thread-deflector protrusions 12 have an essentially wedge-shaped cross-section, preferably without sharp edges, as illustrated by FIGS. 3 and 4. FIGS. 3 and 4 show sections parallel to the base sheet 1 at the level of arrows A and B, respectively, from FIG. 2. In the embodiment, the thread-deflector protrusions 12 extend as far as the upper rim of the wall 3.

A first lip 14 which is matched to the course of the wall 3 extends downwards from the cover 9, and lies against the outward-facing side 10 of the wall 3 when the cover 9 is fitted, as can be seen from FIGS. 2 and 4. In the region of the thread-deflector protrusions 12 the first lip 14 is provided with recesses 15 into which the thread-deflector protrusions 12, which extend as far as the upper rim of the wall 3, project. Parallel to the first lip 14, the cover 9 has a second lip 16 which lies against the inward-facing side 17 of the wall 3 when the cover 9 is fitted. In the embodiment, the second lip 16 does not have gaps corresponding to the recesses 15, see FIG. 4.

The first lip 14 and the second lip 16 enclose the upper section of the wall 3, see FIG. 2, and thus offer a secure fixing for the wall 3 through the cover 9. As a result of the interplay between the thread-deflector protrusions 12 and the first lip 14, the possibility of a surgical thread sticking in the border region between the wall 3 and the cover 9 as the thread is being removed from the packaging is reliably avoided. Should it move in the direction of the cover 9, the thread is kept away by the thread-deflector protrusions 12 from any gap between the first lip 14 and the wall 3.

In order to connect the cover 9 to the wall 3, in the embodiment projections 18 start from a number of points on the wall 3 and pass through assigned openings in the cover 9, see FIG. 2. The ends of the projections 18 are deformed in the manner of rivets after the cover 9 has been fitted onto the base sheet 1 with the wall 3. Other and/or additional types of connection between the wall 3 and the cover 9 are possible. Thus, e.g., the use of catches, which project at the periphery of the cover 9 and engage with suitable counterparts at the wall 3, is conceivable.

Figure 5:
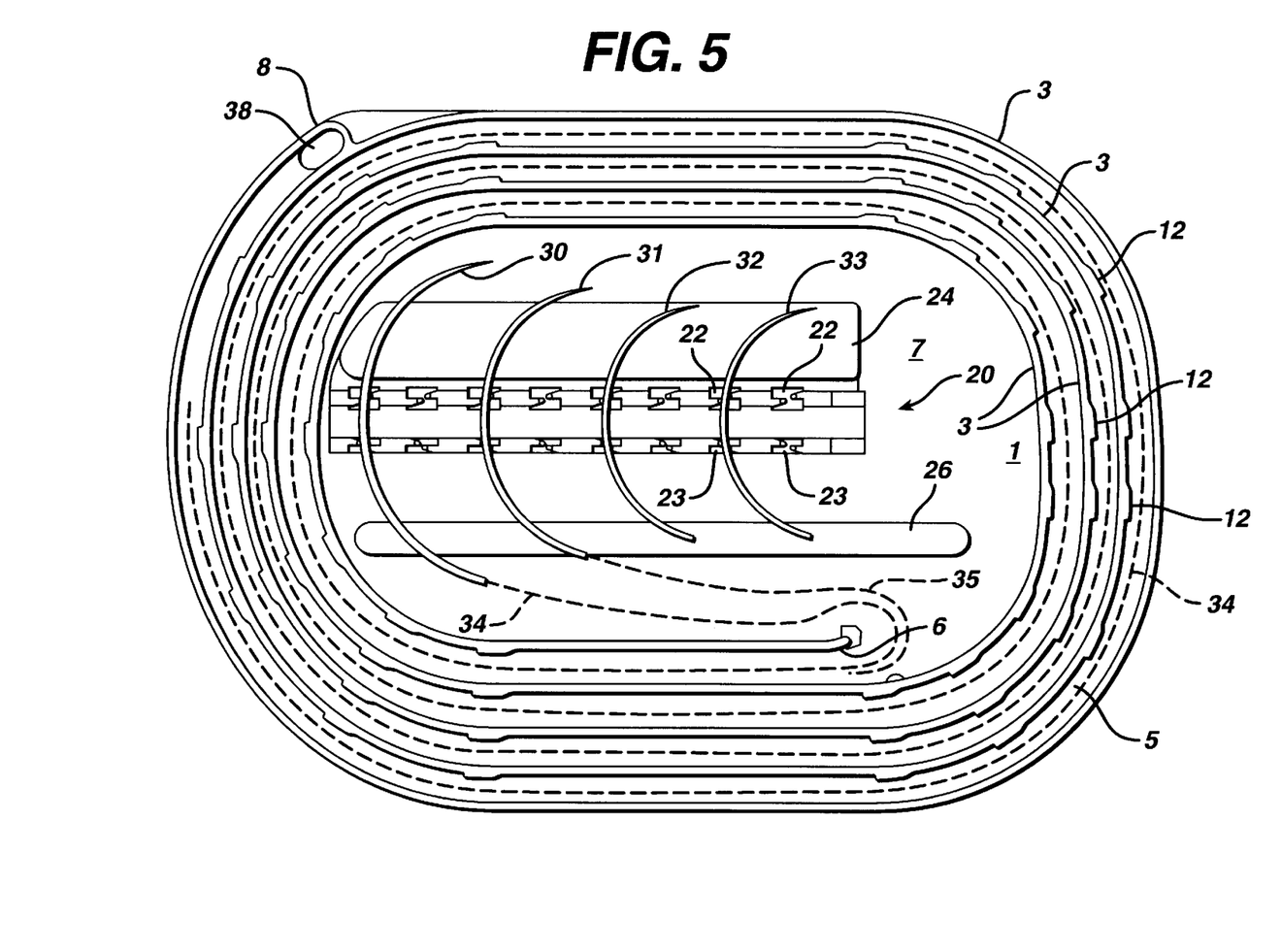

The first version of the packaging, and the second version which is very similar to it, are intended for surgical suture material which consists of surgical threads to one end of each of which a surgical needle is secured. As FIGS. 1 and 5 show, in both versions a mounting 20 for holding several surgical needles is arranged in the thread-removal area 7. For each surgical needle, the mounting 20 has a first two-part clamp 22 and a second two-part clamp 23, each of which consists of two clamp parts which project upwards in the manner of prongs and are elastically designed vis-à-vis each other. The first two-part clamps 22 and the second two-part clamps 23, respectively, are arranged in a row, as can be seen from FIGS. 1 and 5. A surgical needle can be inserted from above into the first two-part clamp 22 and second two-part clamp 23 assigned to it and is thereafter in the position represented in FIG. 5. A supporting surface 24 projecting vis-à-vis the base sheet 1 supports the surgical needles in the region of their tips, while a supporting strip 26 extending parallel to the rows of the first and second two-part clamps 22, 23 makes it easy to remove the surgical needles from the packaging and prevents the surgical needles from tilting. Other designs of the mounting for holding surgical needles are conceivable. For example, just one two-part clamp can be assigned to each surgical needle.

Four needles 30, 31, 32 and 33, represented in different sizes for the purposes of illustration, are drawn in FIG. 5. Other needle types, say straight surgical needles, can also be housed by the packaging. The surgical thread 34 belonging to needle 30 is shown in its full length by means of dotted lines in FIG. 5. It extends almost as far as the second end 8 of the thread duct 5. The route of the thread 35 starting from needle 31 is indicated only as far as the first end 6 of the thread duct 5 in FIG. 5; the other threads are not shown, in the interests of clarity. However, all the threads run in the thread duct 5. The dimensions of the thread duct 5 are large enough for the other threads in the thread duct 5 to neither cause nor suffer disturbance when a surgical thread is removed.

In the embodiment, the packaging is packed with surgical suture material after the thread duct 5 has been closed by fitting of the cover 9. In the region of the second end 8 of the thread duct 5, the base sheet 1 has an opening 38, see FIG. 5. The thread duct 5 can be brought into contact with a source of negative pressure via the opening 38. The ends of the surgical threads that are to be introduced into the packaging are brought to the first end 6 of the thread duct 5 and then sucked into the thread duct 5 with the help of the source of negative pressure. This functions quickly and reliably, with the surgical threads distributing themselves evenly along the thread duct 5, as indicated in FIG. 5. In particular, the thread-deflector protrusions 12 do not represent an obstacle for the ends of the surgical threads during the packing process, if, as is shown in FIGS. 3 and 4, they are of wedge-like design, with the result that the ends of the surgical threads can slide along them without problems.

In order to remove surgical suture material from the packaging represented in FIG. 5, the desired surgical needle, e.g. needle 30, is gripped with a needle holder in the section between the second two-part clamp 23 and the supporting strip 26 and detached from the mounting 20. The supporting strip 26 prevents the needle 30 from tilting over. The surgical thread 34 is then drawn out of the thread duct 5 by pulling on the needle 30. The other surgical threads, e.g. thread 35 or the threads drawn in in FIG. 2, do not interfere, and change their position only slightly when thread 34 is pulled out of the thread duct 5. As a result of the forces which occur when the thread 34 is pulled out, thread 34 is forced towards the outward-facing side 10 of the wall 3. The thread-deflector protrusions 12 prevent the thread 34 from being rubbed against the wall 3 along the whole of its length situated in the thread duct 5. The removal of the thread is made much easier as a result. As has already been explained, because of the thread-deflector protrusions 12 it is impossible for the thread 34 to enter any gap or a small crack between the cover 9 or the first lip 14 and the wall 3 and stick there. The removal of a surgical thread is made yet easier if, in the course of the thread duct 5, the transitions between the base sheet 1 and the wall 3 and/or the transitions between the wall 3 and the cover 9 or the first lip 14 and the second lip 16 and/or the transitions between the first lip 14 and second lip 16, respectively, and the cover 9 are of a rounded design, as indicated in FIG. 2.

As can be seen from FIGS. 3 and 4, the thread-deflector protrusions 12 have an essentially wedge-shaped form in the embodiment, the apex of the wedge angle in question pointing towards the first end 6 of the thread duct 5, and they extend essentially perpendicular to the base sheet 1. In other words, the cross-section of the thread-deflector protrusions 12 essentially has, in the representation according to FIG. 3 or FIG. 4, the shape of an acute-angled triangle with the acute angle towards the first end 6 of the thread duct 5. However, other designs of the thread-deflector protrusions are conceivable, for example those with an essentially rectangular cross-section.

In the embodiment of FIGS. 1 to 5, the base sheet 1, the wall 3 with the thread-deflector protrusions 12 formed thereat and also the mounting 20 for holding surgical needles including the supporting surface 24 and the supporting strip 26 are made in one piece as an injection moulding, preferably from polypropylene or polyethylene. The cover 9 with the first lip 14 and the second lip 16 is also a one-piece injection moulding, which preferably consists of the same material as the injection moulding with the base sheet 1. The two parts are joined together with a precise fit after they have been produced and riveted to each other at the protrusions 18, as has already been explained with reference to FIG. 2.

FIGS. 6 to 9 show a third version of the packaging for surgical suture material. This version is intended for surgical suture material which consists of surgical threads only, i.e. has no needles. The structure of the third version is essentially the same as that of the first two versions, for which reason the same reference numbers are used in FIGS. 6 to 9 as in FIGS. 1 to 5. Unlike the first two versions, however, the third version has no mounting for holding surgical needles, but a ramp 40 developed in one piece from the base sheet 1. The ramp 40 is shown magnified and in perspective in FIG. 7 in the area of the zone designated Z in FIG. 6. A tongue 41 starting from the cover 9 projects into a recess formed at the top of the ramp 40, see FIG. 6 and FIG. 7. To both sides of the ramp 40, the cover 9 juts out over the thread-removal area 7, with the result that two protrusions 42 and 43 are formed which serve as thread holders.

Figure 6:
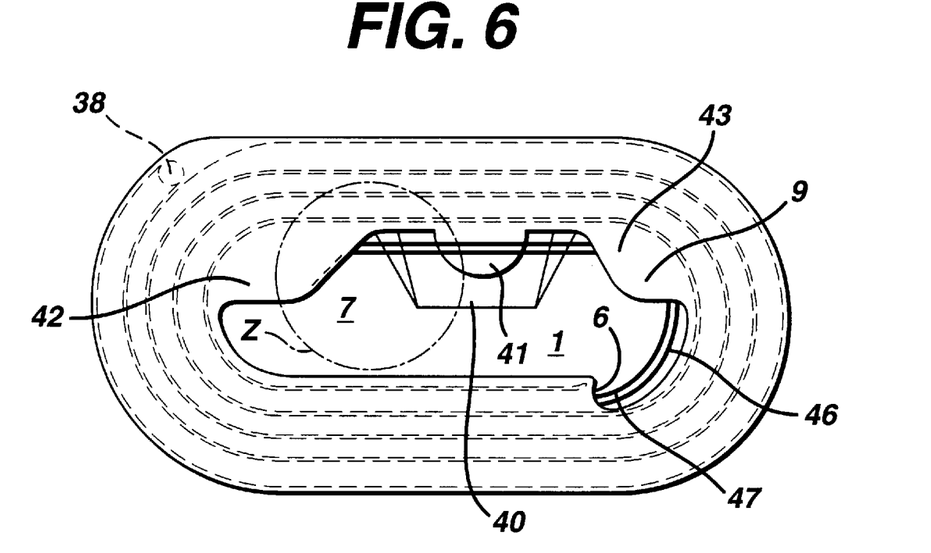
Figure 7:
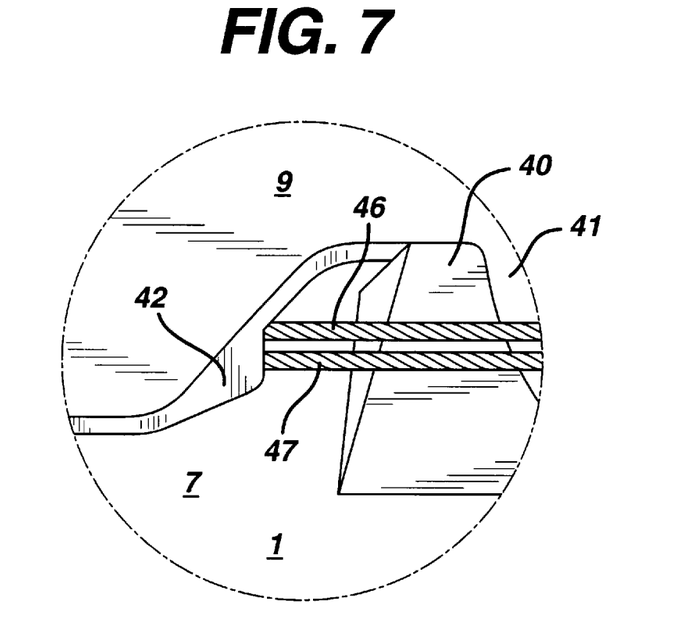

It can be seen from FIGS. 6 and 7 how the front sections of e.g. two surgical threads 46 and 47 projecting from the thread duct 5 are guided inside the thread-removal area 7 and clamped between the ramp 40 and the two protrusions 42 and 43. Therefore, the front ends of the threads 46 and 47 do not project upwards over the cover 9. If surgical threads are to be removed from the packaging, the operator rolls the threads (threads 46 and 47 in this case) up over the ramp 40 with his thumb, i.e. onto the cover 9. In the process, the threads run over the tongue 41, which for this purpose is lowered far enough into the aforementioned recess in the ramp 40 for the threads to be able to move to the top of the cover 9 and not become stuck in any gap between the ramp 40 and the cover 9. The bundle of threads formed by the threads fans out in the process, and the front ends of the threads are no longer covered by the protrusion 42. The threads are now individually accessible without further ado, and the operating surgeon can grasp a desired thread with forceps or another suitable instrument and pull it out of the packaging in the way that has already been described in connection with FIGS. 1 to 5.

Figure 8:
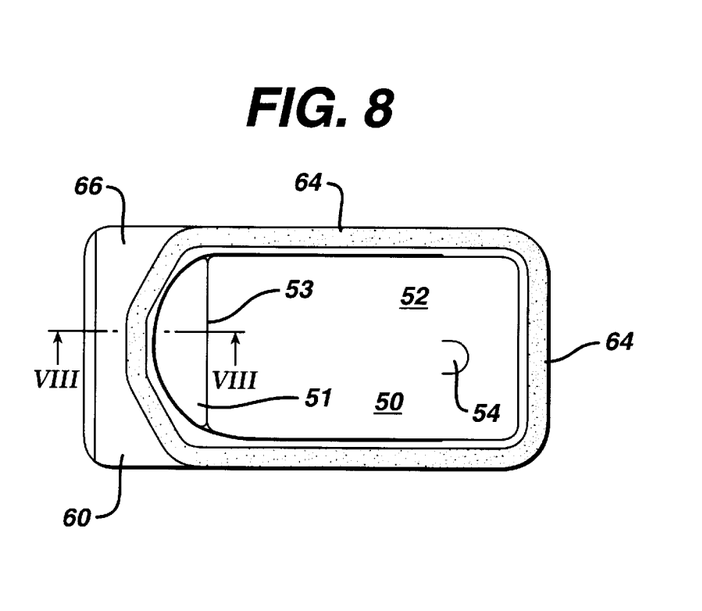
Figure 9:
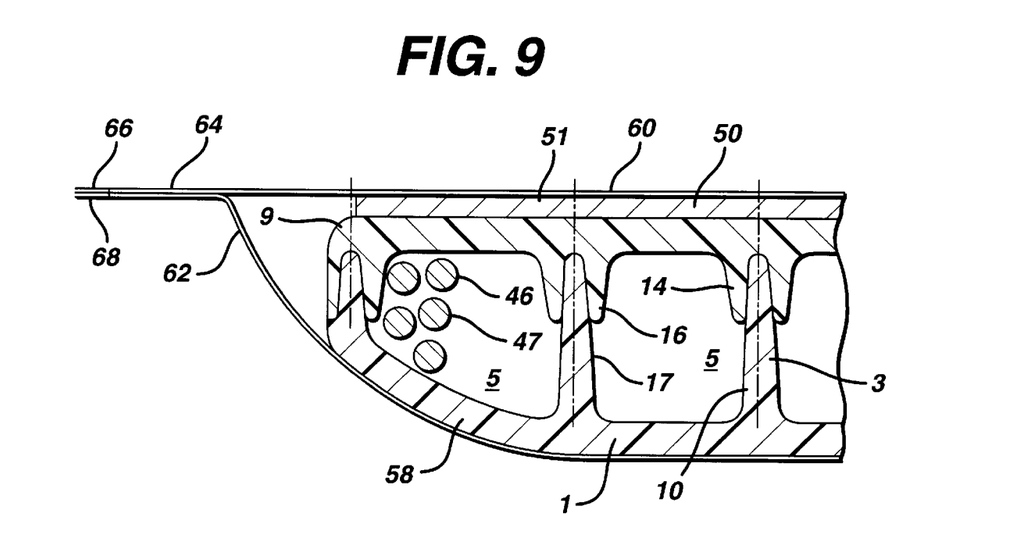

FIGS. 8 and 9 show a top layer 50 which is arranged above the thread-removal area 7 and protects the thread-removal area 7 before the packaging is used. In the embodiment, the top layer 50 is made from cardboard and has a securing section 51 and a section 52. The securing section 51 is glued on the cover 9. The section 52 covers the thread-removal area 7 and can be folded back along a fold line 53 in order to make the thread-removal area 7 accessible. To facilitate a better grip on the section 52, the top layer 50 juts out over the cover 9. In the embodiment, the section 52 is locked above the thread-removal area 7 by means of a downwardly projecting nose 54 at the edge of the recess. If a perforation line is used instead of the fold line 53, the section 52 can be torn off without problems from the securing section 51. The previously described versions of the packaging for surgical suture material can also have a top layer 50.

In an alternative version, the top layer 50 is fixed to the packaging, without being glued, with the help of locking noses, which preferably start from the top layer 50. For example, the locking noses can engage at the cover 9 at the edge of the recess above the thread-removal area 7. The top layer 50 can then be removed upwards without problems if access to the thread-removal area 7 is desired.

In order to guarantee the sterility of the packaging and of the surgical suture material contained in it, an envelope enclosing the packaging is provided, which is shown in FIGS. 8 and 9. In the embodiment, the envelope has an upper layer 60, which is situated above the cover 9 and the top layer 50, and a lower layer 62, which extends on the underside of the base sheet 1 and along its edge zone 58 which is turned upwards in the third version. The upper layer 60 and the lower layer 62 are glued to each other at a circumferential jointing edge 64. The upper layer 60 and the lower layer 62 continue beyond the jointing edge 64 as an upper grip projection 66 and a lower grip projection 68, respectively. The upper grip projection 66 and the lower grip projection 68 are not glued to each other.

The envelope is preferably made from aluminium foil or aluminized foil. To open the envelope, an assistant not working under sterile conditions grasps the upper grip projection 66 with one hand and the lower grip projection 68 with the other hand and pulls part of the upper layer 60 from the lower layer 62, without in the process touching the packaging that lies inside. The opening created in this way is large enough, and also sufficiently dimensionally stable because of the material used for the envelope, for the operating surgeon who is working under sterile conditions to be able to grasp the packaging through the opening without coming into contact with the non-sterile outsides of the upper layer 60 and of the lower layer 62.

The packaging for surgical suture material can be produced in many variants. The shape of the packaging is preferably matched to the provided surgical suture material, e.g. the length of the thread duct 5 to the length of the surgical threads that are to be packed.

We claim:

1. A package for surgical suture material, having a base sheet (1) and a spiral wall extending from said base sheet, said wall defining a thread duct (5) which opens at its first end (6) into a thread-removal area (7), and having a cover (9) for the thread duct (5), the wall (3) being provided on its outward-facing side (10) with thread-deflector protrusions (12) spaced apart from one another in the course of the thread duct (5) wherein said cover (9) has a lip (14) matched to the course of the wall (3), which lip rests against the outward-facing side (10) of the wall (3) in the thread duct (5) and is provided in the region of the thread-deflector protrusions (12) with recesses (15) into which the thread-deflector protrusions (12) project.

2. Packaging for surgical suture material according to claim 1, characterised in that, parallel to the lip (14), the cover (9) has a second lip (16) which rests against the inward-facing side (17) of the wall (3) in the thread duct (5).

3. The package for surgical suture material according to claim 1, characterised in that the thread-deflector protrusions (12) have a wedge, configuration, wherein each protrusion has an object and a wedge angle, wherein the apex of the wedge angle in question points towards the first end (6) of the thread duct (5).

4. Packaging for surgical suture material according to claim 1, characterised in that, in the course of the threat duct (5), the transitions between the base sheet (1) and the wall (3) and/or the transitions between the wall (3) and the cover (9) are of rounded design.

5. Packaging for surgical suture material according to claim 1, characterised in that the base sheet (1) and the cover (9) has an opening (38) in the region of the second end (8) of the thread duct (5).

6. Packaging for surgical suture material according to claim 1, characterised in that the thread-removal area (7) is arranged in the zone surrounded by the thread duct (5).

7. Packaging according to claim 6, characterised in that the cover (9) at least partially leaves open access to the thread-removal area (7).

8. Packaging for surgical suture material according to claim 1, characterised in that, in the thread-removal area (7), a wedge-shaped ramp (40) is arranged at the base sheet (1), which ramp is preferably designed in one piece with the base sheet (1) and preferably has a thread holder (42, 43) assigned to it.

9. Packaging for surgical suture material according to claim 8, characterised in that a tongue (41) starting from the cover (9) projects into a recess arranged at the ramp (40).

10. Packaging for surgical suture material according to claim 1, characterised in that, in the thread-removal area (7), a mounting (20) for holding one or more surgical needles (30–33) is arranged at the base sheet (1), which mounting is formed in one piece with the base sheet (1).

11. Packaging for surgical suture material according to claim 10, characterised in that a supporting strip (26) for at least one surgical needle (30–33) is arranged at the base sheet (1), which strip is preferably formed in one piece with the base sheet (1).

12. Packaging for surgical suture material according to claim 1, characterised in that the thread duct (5) is designed to house several surgical threads (34, 35; 46, 47).

13. Packaging for surgical suture material according to claim 1, characterised in that the base sheet (1) and the wall (3) are designed integral with each other.

14. Packaging for surgical suture material according to claim 14, characterised in that the cover (9) and the wall (3) are connected to each other by means of catches and/or protrusions (18), preferably shaped like rivets, engaging in recesses.

15. Packaging for surgical suture material according to claim 1, characterised in that a top layer (50) is provided over the thread-removal area (7).

16. Packaging for surgical suture material according to claim 1, characterised in that an outer envelope (60, 62) guaranteeing sterility is provided for the packaging.

17. Packaging for surgical suture material according to claim 1, characterised by surgical suture material (30–33, 34, 35; 46, 47) contained in the packaging.

18. A package for surgical suture material, comprising a base sheet, and a spiral wall extending from said base sheet, said wall defining a thread duct (5) which opens at its first end (6) into a thread-removal area (7), and having a cover (9) for the thread duct (5), the wall (3) being provided on its outward-facing side (10) with thread-deflector protrusions (12) spaced apart from one another in the course of the thread duct (5), wherein said cover (9) has a lip (14) matched to the course of the wall (3), which lip rests against the outward-facing side (10) of the wall (3) in the thread duct (5) and is provided in the region of the thread-deflector protrusions (12) with recesses (15) into which the thread-deflector protrusions (12) project, wherein parallel to the lip (14), the cover (9) has a second lip (16) which rests against the inward-facing side (17) of the wall (3) in the thread duct (5), and the thread-deflector protrusions (12) have a wedge configuration wherein each protrusion has an apex and a wedge angle, and wherein the apex of the wedge angle in question points towards the first end (6) of the thread duct (5).

* * * * *